Figure 1:
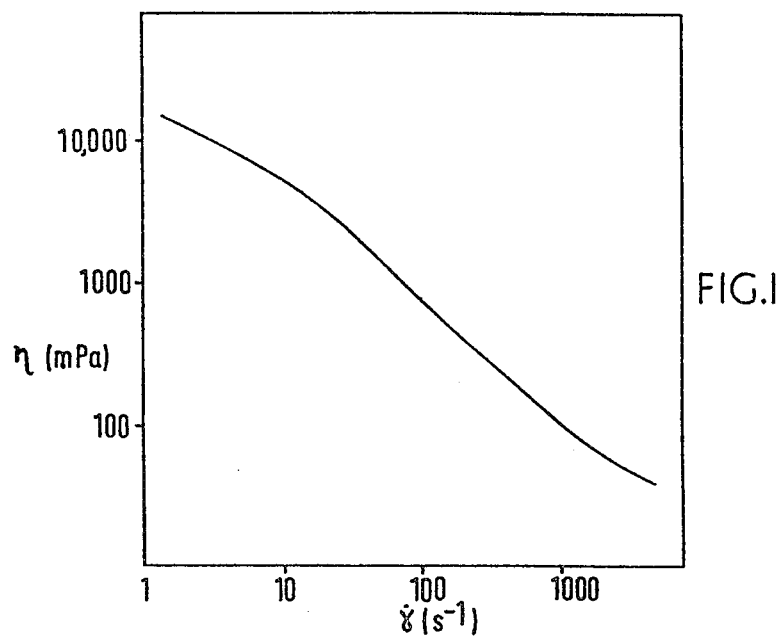

United States Patent [19]

Lawson et al.

[11] 4,372,785
[45] Feb. 8, 1983

[54] SUSPENSIONS AND GELS OF INDICAN AND THEIR USES

[75] Inventors: Christopher J. Lawson, Reading; Kenneth C. Symes, Wokingham, both of England

[73] Assignee: Talres Development (N.A.) N.V., Netherlands Antilles

[21] Appl. No.: 354,210

[22] Filed: Mar. 3, 1982

Related U.S. Application Data

[62] Division of Ser. No. 126,311, Feb. 29, 1980, Pat. No. 4,338,432.

[30] Foreign Application Priority Data

Mar. 6, 1979 [GB] United Kingdom ............... 7907786

[51] Int. Cl.$^3$ ........................ C08L 1/08; C08L 5/00
[52] U.S. Cl. ............................. 106/170; 106/197 R; 106/197 C; 106/205; 106/208; 252/312; 252/315; 426/573
[58] Field of Search ............... 106/205, 208, 197, 170; 435/101; 426/573; 252/312, 315

[56] References Cited

U.S. PATENT DOCUMENTS 4,338,432 7/1982 Lawson et al. ................ 435/101

OTHER PUBLICATIONS

Chem. Abst.; 94:45596f, Lawson et al.

Primary Examiner—Theodore Morris
Attorney, Agent, or Firm—Ostrolenk, Faber, Gerb & Soffen

[57] ABSTRACT

Indican, a polysaccharide comprising (1→3) glucose, (1→4) mannose, (1→4) rhamnose and (1→3 or 4) -0-(1-carboxyethyl)rhamnose units in a molar ratio of about 2:1:1-2:1 respectively; containing 12-15% by weight acetyl units $[\alpha]_D^{20}$ about $-61°$; having principle absorption bands in the infra red band at 3390, 1735, 1615, 1375, 1250 and 1050 cm$^{-1}$; a solubility of at least 1% by weight in methanol and in ethylene glycol, and an inherent viscosity of about 33.5 dl/g. has useful thixotropic properties and provides a method of modifying the viscosity of a liquid by incorporating indican therein. The liquid may be aqueous or organic solvent-based. Thickened and stabilised products are also provided.

14 Claims, 2 Drawing Figures

SUSPENSIONS AND GELS OF INDICAN AND THEIR USES

This application is a division of U.S patent application Ser. No. 126,311, dated Feb. 29, 1980, U.S. Pat. No. 4,338,432.

This invention relates to the use of a microbial polysaccharide as a suspending, emulsifying or gelling agent.

Various polysaccharides are known which have the ability to modify the viscosity of an aqueous medium in order to confer pseudoplasticity. Pseudoplasticity, and also thixotropy, and a high yield stress are valuable characteristics in many fields, for example in emulsion paint manufacture, in agricultural sprays, in well-drilling fluids and so on. In this specification, the term thixotropy is intended to mean the characteristic of lowering of viscosity of liquids when subjected to shear. Pseudoplasticity is regarded as the particular case where the regaining of viscosity is extremely rapid.

Xanthan gum exhibits some activity in this respect, particularly when admixed with galactomannan gums, but its viscosity is too rapidly regained for some purposes.

A microbial polysaccharide which possesses useful characteristics of this type is described in U.S. Pat. No. 3,960,832. This polysaccharide, known as Heteropolysaccharide 7, is derived from *Azotobacer indicus* var. *myxogenes*. This polysaccharide has been proposed for use in emulsion paints, for example in U.S. Pat. No. 3,894,876 and in well-drilling fluids, for example in British patent specification No. 1,416,013.

We have now obtained, from a different microbial source, a new microbial polysaccharide which is chemically different from Heteropolysacchride 7 but which possesses a rheology giving it similar uses, together with other important properties not shared by Heteropolysaccharide 7.

The polysaccharide according to the present invention is derived from a microorganism deposited at the American Type Culture Collection under the No. ATCC 19361 by H. Jensen in 1957. The microorganism was originally deposited under the name *Azotabacter lacticogenes*. However, in the latest edition of Bergey's Manual of Determinative Bacteriology (8th Edition 1974), *A. lacticogenes* is no longer recognised as a separate species, but, together with *Beijerinckia lacticogenes* and several other species is now classified as *B. indica*. The nomenclature of the microorganisms in question is thus rather complex and is apt to be misleading. We have compared the microorganism ATCC 19361 with the type strain of *B. indica*, deposited as NCIB 8712, and also, for reference, with *A. indicus* var. *myxogenes* ATCC 21423. From our experiments, it is clear that the microorganism deposited as ATCC 19361 should, in fact, be classified as a strain of *B. indica*, and will now be referred to in this specification as *B. indica* ATCC 19361. From our experiments, it is also clear that *A. indicus* var. *myxogenes* ATCC 21423 differs significantly from both the other organisms tested. It is indeed a species of *Azotobacter* rather than *Beijerinckia* since:

(i) it grows readily in nutrient broth and on nutrient agar;
(ii) it forms a pellicle in most liquid media; and
(iii) it forms a yellow non-water soluble pigment.

Details of the comparison are given later in this specification.

The polysaccharide according to the present invention is the polysaccharide obtained by culture of *B. indica* ATCC 19361 in a nutrient medium and then subsequently precipitating the polysaccharide produced, e.g. by addition of an alcohol such as isopropyl alcohol or by rendering the medium acid. The invention also comprises a substantially identical polysaccharide if produced from a different microbial source. This polysaccharide will, for convenience, be referred to hereinafter as indican.

The type strain of *B. indica* is *B. indica* Starket and De, ATCC 9039 which is identical to NCIB 8712. This strain was reported by Quinnell et al. (Can. J. Microbiol. 3 (1957) 277) to produce a polysaccharide comprising units of glucose, glucuronic acid and a heptose. Haug and Larsen (Acta. Chem. Scand. 24 (1970) 1855) reported that the uronic acid was, in fact, gluronic acid. Lopez and Backing (Microbiol. Espana 21 53) showed that *B. indica* strain Hawaii-2 produces a polysaccharide which comprises units of glucose, galactose and mannose and glucuronic and galacturonic acid, and this combination is cited by Bergey (8th Edition) for the polysaccharide produced by *Beijerinckia*.

Sowa, in a Ph.D. thesis at Queens University, Canada, in 1962, indicated that a strain of "*B. lacticogenes*" produced a polysaccharide comprising units of glucose, uronic acid, rhamnose and mannose (in order of decreasing concentration). In contrast, indican comprises units of glucose, mannose, rhamnose and a carboxyethyl rhamnose, while Heteropolysaccharide 7, derived from *Azotobacter indicus* var *myxogenes*, comprises units of glucose, rhamnose and a uronic acid. Indican is also soluble in methanol at 1% by weight, whereas Heteropolysaccharide 7 is quite insoluble in methanol at that concentration. This solubility in non-aqueous solvents gives indican additional uses of considerable interest.

The present invention utilises indican, a polysaccharide comprising (1→3) glucose, (1→4) mannose, (1→4) rhamnose and (1→3 or 4)0-(1-carboxyethyl)- rhamnose units in a molar ratio of about 2:1:1–2:1 respectively, containing 12–15% by weight acetyl units, $[\alpha]_D^{20}$ about $-61°$, having principle absorption bands in the infra red band at 3390, 1735, 1615, 1375, 1250 and 1050 cm$^{-1}$, a solubility of at least 1% by weight of at least 1% by weight in methanol and in ethylene glycol, and an inherent viscosity of about 33.5 dl/g, and especially substantially cell-free indican obtained from a culture of *Beijerinckia indica* ATCC 19361.

According to the present invention, there is provided a method of modifying the viscosity of a liquid, especially, a polar liquid, by incorporating therein an effective amount of indican.

According to one feature of the present invention, there is provided a method of modifying the viscosity of an aqueous fluid, particularly rendering it pseudoplastic, by incorporating therein at effective amount of indican.

According to another feature of the present invention, there is provided a method of suspending a particulate solid in an alcoholic medium by incorporating in the medium an effective amount of indican.

Another feature of the present invention, is a method of gelling that cooking liquor around a meat product or the like by incorporating therein an effective amount of indican.

According to another feature of the invention, there is provided a thixotropic, thickened liquid containing indican substantially free from cells of *B. indica*, especially an aqueous liquid.

According to another feature of the invention, there is provided a suspension of a particulate solid in an alcoholic medium containing indican. In particular, there is provided a suspension of xanthan gum in an alcoholic medium containing indican. Alginate and CMC can also be suspended.

According to another feature of the invention, there is provided an aqueous emulsion of a hydrophobic liquid, in particular an oil or petroleum product, or of a water-in-oil type of emulsion, containing indican as an emulsifying agent.

According to another feature of the invention, there is provided a canned food product, particularly meat or a meat-like product, in a jelly containing indican.

According to another feature of the invention, there is provided a paint stripper composition containing a paint solvent together with indican as a thickener.

According to another feature of the invention, there is provided a flexible film of indican formed by evaporating the solvent from a thin layer of an indican solution. Such a film has uses in a wide range of fields from painting to metal foil manufacture.

In any of the above uses, the amount of Indican will vary depending on the results required. In general, an amount of 0.01% to 2% by weight can be used. For emulsification, gelling and suspension of solids in alcohols, a proportion of 0.1 to 0.5%, particularly about 0.25% by weight is advantageous.

The ability of indican to thicken and render pseudoplastic an aqueous medium means that the polysaccharide is of particular interest as a thickening agent in a number of different applications. One particularly important field is that of aqueous emulsion paints, which are desirably formulated in a non-drip form. In general, an amount of from 0.01 to 2% by weight of indican can be incorporated in the aqueous emulsion, together with the conventional latex of film-forming resin and pigments. Other components of the paint may be the conventional extenders, anti-foaming agents, dispersion agents, thermal stabilisers and preservatives. The latex may comprise a styrene-butadiene copolymer, a polystyrene, a polyacrylate or polyvinylacetate emulsion, all of which are conventional in paint technology.

Another use for the thickening effect is in well-drilling fluids based on water or brine. In this case, the ability to thin under applied shear enables the fluid to lubricate at areas of high shear, while areas of low shear the viscosity and gel strength enable drill clays and weighting agents to be entrained and suspended. The emulsifying effect of the polysaccharide also enables the oil to be emulsified with water.

Indican may also be used in water flooding, in secondary oil recovery, either in place of or in combination with xanthan gum.

Pseudoplasticity or thixotropy is also an advantage in aqueous sprays, for example of herbicides and pesticides used in agriculture. A thixotropic fluid will be temporarily thinned on spraying but will thicken after contact with leaf surfaces etc. to prevent run-off.

Other uses in aqueous media include stabilisation of aqueous suspensions of pigments and minerals in ceramic glazes, in textile printing pastes and in many other uses where conventional thickening and thixotropic agents are used.

A particularly noteworthy feature of indican is its relatively high solubility in lower alkanols and aqueous alcoholic systems. One particularly important utility provided by this solubility is as follows.

Xanthan gum is now widely used in drilling and water flooding operations in the oil industry in the form of dilute aqueous solutions. The dry xanthan gum is in the form of a powder which is very difficult to disperse in water. Concentrated aqueous solutions would gel and would be unsuitable. Two main solutions to this problem are in current use. Firstly, the xanthan is suspended as a slurry in liquid paraffin or another water immiscible solvent, together with a suspension stabiliser and an emulsifier. This suspension can be added to the water and the emulsifier disperses the water immiscible carrier evenly. The resulting xanthan solution, however, is opaque and contains emulsified immiscible solvent which can be undesirable. The alternative procedure is to suspend the xanthan in an alcohol such as ethanol with a stabiliser for the suspension. Alcohol suspensions of this type are easily dispersible in water to give a homogeneous solution. The stabiliser generally used for the alcohol suspensions is a cellulose derivative, for example a hydroxypropyl cellulose, in combination with a gelling agent. An example of this type of suspension is given in U.S. Pat. No. 3,894,879. However, the hydroxypropyl cellulose derivative and its gelling agent are relatively inefficient, even when used at relatively high levels, e.g. about 1%.

According to the present invention, indican can be used to stabilise an alcoholic or aqueous alcoholic suspension of xanthan gum in the absence of a cellulose derivative or gelling agent, at a much lower concentration, for example of the order of 0.25% by weight of the suspension medium. Alcohol suspensions of this type are thixotropic and stable on storage and thus can be easily transported either in containers or by pump. The suspensions disperse easily in water.

Indican also has uses as an emulsifying agent and thus is of interest in stabilising xanthan gum suspensions in liquid paraffin and other water immiscible solvents. It is also of particular interest in the emulsification of kerosene with water, for example in herbicidal and pesticidal sprays, where, as explained above, it serves the added purpose of preventing run-off.

The property of film formation possessed by indican renders it of considerable interest in any field where a cast polysaccharide film is desirable. The gum can be dissolved in a volatile solvent such as methanol/methylene chloride mixture and allowed to dry on a smooth surface. The film can be stripped off as a flexible material. The solubility in solvents such as methanol/methylene chloride also renders indican very suitable for use in thickened paint stripper formulations.

Finally, indican possesses the property of dissolving in a solvent such as water to form a viscous solution/gel, which remains highly viscous on being heated and becomes a firm gel on recooling. This property means that indican is of particular use in the canning industry, as a replacement for xanthan gum/carob gum mixtures. Chunky meat products, such as pet foods, can be evenly distributed in a jelly, the viscosity of which does not markedly decrease when hot, thus preventing settling of the contents of the can. In this respect, indican is distinctly different from the reported Heteropolysaccharide 7.

As explained earlier, indican may be produced by culture of *B. indica* ATCC 19361. A comparison of *B. indica* ATCC 19361 with the type strain, NCIB 8712 was carried out. At the same time, these two strains were compared with *A. indicus* var *myxogenes* ATCA 21423, the source of Heteropolysaccharide 7.

TABLE 1

Tests used in Comparative Study

| | |
|---|---|
| Cell morphology | Gram stain; spore stain; acid fast stain; capsules; motility. |
| Colonial morphology | YM agar; Burk's agar + glucose; Burk's agar + sucrose. |
| Growth characteristics | Nutrient broth; YM broth; nutrient agar; optimum temperature; pH range; salt tolerance in YM broth. |
| Biochemical characteristics | Methyl red; catalase; indole formation; urease, arginase; oxidase; amylase; cellulase; gelatin liquefaction; nitrate reduction; $H_2S$ formation; citrate utilisation; acetylmethyl-carbinol formation (Voges - Proskauer) |
| Carbohydrate utilisation and acid production | 20 carbon sources used |
| Effect of amino acids on pigmentation and growth | 20 amino acids used |

TABLE 2

Principal Differences Observed

| | Test | *B. indica* type strain NCIB 8712 | *B. indica* ATCC 19361 | *A. indicus* var. *myxogenes* ATCC 21423 |
|---|---|---|---|---|
| 1 | Motility | weakly + | Majority weakly + | strongly + |
| 2 | Growth in E1 medium | clumps | clumps | chains |
| 3 | Urease | − | + | − |
| 4 | Oxidase | weakly + | + | − |
| 5 | Amylase | | | |
| | Starch nut.agar | no growth | no growth | + |
| | YM + starch | − | − | Weak + |
| 6 | Carbohydrate utilisation and acid prodn. | | | |
| | arabinose | +(13 days) | +(13 days) | v. weak + (21 days) |
| | xylose | − or weak + | − or weak + | + |
| | maltose | +(21 days) | − | + |
| | trehalose | − or + | − | + |
| | lactose | − | − | + |
| | cellobiose | − | − | + |
| | melibiose | − | +(21 days) | + |
| | dextran | weak + (21 days) | − | + |
| | mannitol | + | weak + | − |
| 7 | Amino acids: growth and pigment prodn. | | | |
| | DL threonine pigment | growth + cream | growth + cream | growth − yellow |
| 8 | Nutrient broth: growth | − | − | yellow; +; pellicle |
| 9 | Nutrient agar: growth | − | − | yellow; +; 0.5-2 mm |
| 10 | pH range | | | |
| | YM broth | 4.6-7.2 | 4.6-7.2 | 4.6-7.2 |
| | Nut. broth | + only at 7.4-7.9 | + only at 7.9 | 3.9-7.9 |
| 11 | Salt tolerance % | weak at 1% | 0.4% +; 0.6% − | + at 1.6; weak at 2.0 |

It will be seen that ATCC 19361 bears a close resemblance to NCIB 8712 and may be classified as *B. indica* according to Bergey (8th Edition). On the other hand, *A. indicus* var. *myxogenes* ATCC 21423 is probably correctly classified as a species of Azotobacter because of its ready growth in nutrient broth and on nutrient agar, its formation of pellicle in most liquid media, and the production of a yellow water-insoluble pigment.

DESCRIPTION OF ATCC 19361

Cell Morphology

Size: 0.5-1.2 m by 1.6-3.0 m.

Shape: Straight or slightly curved rods. Characteristic large, highly refractile lipoid bodies occurring at each end of cell, which persist in aged cultures.

Resting stages: Neither cysts nor spores observed.

Gram reaction: Negative.

Acid fast Stain: Negative.

Motility: Most negative, a few weakly positive.

| Colonial Morphology | |
|---|---|
| YM Agar (27° C. 6 days): | Tenacious gum, cream colonies smaller than type strain, circular, entire, domed, opaque, up to 3mm diameter. |
| Burk's medium + glucose (27° C. 6 days): | Punctiform colonies less than 1mm diam. circular, entire, domed. Inoculation point-thick white tenacious elastic gum. |
| Burk's medium + Sucrose (27° C. 6 days): | Punctiform colonies, translucent. Inoculation point - dense growth watery gum |
| Nutrient Agar (27° C. 14 days): | No growth |
| Malt agar (27° C. 14 days): | Weak growth, punctiform colonies |
| Growth Characteristics | |
| Nutrient broth: | No growth |
| YM broth: | Opaque growth, no pellicle or pigment, becomes viscous on incubation |
| Salt tolerance in YM broth: | Grows well with 0.4% NaCl, no growth with 0.6% NaCl. |
| Temperature range: | 10-35° C., optimum 20-30° C. |
| pH range in YM broth: | pH 3.0 to pH 10.0, optimum pH 4.0-10.0 |
| pH range in Nutrient broth: | will show weak growth at pH 8.0 but not below (after 13 days). |

Atmospheric nitrogen fixed in nitrogen deficient media, molybdenum is required for nitrogen fixation.

In neutral or alkaline media, acid is produced. In very acid media, an alkaline substance is produced which increases the pH of the medium.

| Biochemical Characteristics | |
|---|---|
| Catalase: | positive |
| Oxidase: | positive |
| Methyl Red Test: | negative |
| Indol formation: | negative |
| Urease: | positive |
| Amylase: | negative |
| Gelatin liquefaction: | Negative |
| Nitrate reduction: | positive |
| Citrate utilisation: | negative |
| Acetylmethylcarbonyl formation: CVP test | positive |
| $H_2S$ formation (from thiosulphate): | negative |
| Cellulase: | positive |

| Carbohydrate Utilisation | | | |
|---|---|---|---|
| | Growth | Acid Production | Incubation Time |
| D-glucose | Positive | Positive | 20 days |
| D-mannose | Positive | Positive | 13 days |
| D-galactose | Positive | Positive | 20 days |

| -continued | | | |
|---|---|---|---|
| D-fructose | Positive | Positive | 13 days |
| D-arabinose | Positive | Positive | 13 days |
| D-xylose | Negative | Negative | 20 days |
| L-rhamnose | Negative | Negative | 20 days |
| D-sucrose | Positive | Positive | 13 days |
| adonitol | Negative | Negative | 20 days |
| D-maltose | Negative | Negative | 20 days |
| D-trehalose | Negative | Negative | 20 days |
| D-lactose | Negative | Negative | 20 days |
| D-cellobiose | Negative | Negative | 20 days |
| D-melibiose | Positive | Positive | 13 days |
| dextrin | Negative | Negative | 20 days |
| D-raffinose | Positive | Weak Positive | 20 days |
| salicin | Negative | Negative | 20 days |
| D-mannitol | Positive | Weak Positive | 20 days |
| Na—alginate | Negative | Negative | 20 days |

| Effect of aminoacids on pigmentation & growth | |
|---|---|
| (Burk's + glucose 7 days 27° C.) | |
| DL-alanine | no growth |
| DL-serine | no growth |
| DL-phenylalanine | No growth |
| DL-tyrosine | No growth |
| DL-methionine | No growth |
| L-cystine | No growth |
| DL-tryptophan | No growth |
| L-proline | growth, cream, glistening |
| L-hydroxyproline | good growth, cream, glistening |
| DL-aspartic acid | no growth |
| L-glutanic acid | very good growth, cream |
| DL-histidine | no growth |
| L-lysine | poor growth, off white |
| L-arginine | growth, cream |
| L-citrulline | good growth, cream gummy |

The preparation of indican may be achieved by culturing the indican-producing microorganism, e.g. *B. indica* ATCC 19361, either in a batch process or in a continuous process, according to established microbiological techniques. The fermentation medium must be one which is a nutrient for the strain, and in which the strain will successfully produce indican. A typical medium given in Example 1 below, Burk's high phosphate medium, is based on a defined mixture of sucrose and simple inorganic salts. A complex medium, such as nutrient broth or tryptone broth, is also suitable. The microorganism is capable of fixing nitrogen and so a nitrogen-free medium can be used, provided the culture is sufficiently aerated. Alternatively, in addition to aeration, a fixed nitrogen source such as ammonia can be included in the medium. Apart from these considerations, the medium should contain all the essential factors needed for growth and polysaccharide production, including sources of carbon and energy such as sucrose, phosphorus, magnesium and trace elements. The culture may, as indicated above, be batchwise or continuous. Batchwise working is, by its nature, intermittent and capital intensive and commercial production favours continuous working.

The indican can be isolated from the culture by precipitation, e.g. with a water-miscible solvent such as isopropanol. Because of the relatively high solubility of indican in aqueous organic solvents, a higher proportion of precipitant is needed than for, say, xanthan. Alternatively, the suspended matter in the culture, e.g. cells, can be removed by filtration or centrifugation and the polysaccharide obtained by removing the water, e.g. by free-drying.

The following examples illustrate the invention further.

EXAMPLE 1

Production of indican from *B. indica* ATCC 19361

100 ml of sterile growth medium (Table 3) in a 500 ml conical flask was inoculated with the *Beijerinckia indica* ATCC 19321 from a stock culture maintained on growth medium solidified with agar (1.3%). The flask was incubated at 30° C. for 10 days with shaking on a gyrotary shaker (150 rpm).

The shake-flask culture was used to inoculate 4 l of growth medium in a 5 l capacity stirred tank fermentation vessel. The culture was maintained at 30° C., aerated at 2 l min$^{-1}$ and stirred at an impeller speed of 400 rev min$^{-1}$. After 100 h, the contents of this vessel was transferred aseptically into 40 l of culture medium in a 50 l capacity stirred-tank fermentation vessel. The culture was maintained at 30° C., aerated at 10 l min$^{-1}$ and stirred at 100 rev. min$^{-1}$. As the fermentation proceeded and the viscosity increased, the impeller speed was increased to 150 rev min$^{-1}$ 88 h after inoculation and to 210 rev min$^{-1}$ 102 h after inoculation, 117 h after inoculation the apparent viscosity of the culture broth had increased to 12,000 cp at a shear rate of 1 sec$^{-1}$ as measured on a Wells-Brookfield cone and plate microviscometer. At this time, the fermentation broth was added with mixing to isopropanol (4 volumes). The mixture was left until a distinct precipitate formed (8 days). The precipitate was then collected, pressed in muslin to remove excess liquor and freeze dried to yield 200 g of product.

TABLE 3

| Culture Medium Component | Concentration (gl$^{-1}$) |
|---|---|
| Sucrose | 20 |
| K$_2$HPO$_4$ | 0.64 |
| KH$_2$PO$_4$ | 0.16 |
| MgSO$_4$.7H$_2$O | 0.2 |
| NaCl | 0.2 |
| CaCl$_2$.2H$_2$O | 0.043 |
| Na$_2$MoO$_4$ | 1 × 10$^{-3}$ |
| FeSO$_4$.7H$_2$O | 3 × 10$^{-3}$ |
| H$_3$BO$_4$ | 3 × 10$^{-3}$ |
| CoSO$_4$5H$_2$O | 1.2 × 10$^{-3}$ |
| CuSO$_4$.5H$_2$O | 0.1 × 10$^{-3}$ |
| MnCl$_2$.4H$_2$O | 0.09 × 10$^{-3}$ |
| ZnSO$_4$.7H$_2$O | 1.2 × 10$^{-3}$ |

The structure of the polysaccharide, indican, obtained was examined as follows;

Indican (50 mg) was heated with 2 N sulphuric acid for 4 h at 105° C. The solution was neutralised by addition of excess barium carbonate, and the supernatant which formed on centrifuging this mixture de-ionised by treatment with Amberlite IR 120 (H$^+$) and Amberlite 410 (Ac$^-$) resins. On concentration, a syrup was obtained which showed spots on thin layer chromatograms using as the solvent n-BuOH:pyridine water (6:4:3 by volume) corresponding to glucose and rhamnose. A portion of the syrup was converted into the aldonitrile acetate derivatives by heating first with hydroxylamine in pyridine and then with acetic anhydride. Gas chromatographic analysis of the derivatives showed the presence of glucose, mannose and rhamnose in the proportions of 2 glucose:1 mannose:1.6–1.8 rhamnose N.B. The Kelco product Heteropolysaccharide 7 from *Azotobacter indicus* var. *myxogenes* was found to contain glucose and rhamnose only in a ratio of approximately 5 glucose:2 rhamnose.

The presence of an acid component was demonstrated by decarboxylation. On boiling with hydrochloric acid (19% HCl) for 2 h, the carbon dioxide yield as measured by absorption in sodium hydroxide and titration of excess base with hydrochloric acid was 4.1% by weight of the polysaccharide. This tends to imply an anhydrouronate content of about 16%. From these results, it can be concluded that the repeating unit of the polysaccharide is composed of Glc, Man, Rha and an acidic component in the approximate ratio 2:1:2:1. The acid fragment was isolated as a syrup by preparative paper chromatography (6:4:3 nBuOH:pyridine:water, $R_G$ 0.45–0.60) of an acid hydrolysate (1N $H_2SO_4$, 1 h at 100° C.) of cell free indican. The very low colour yield obtained with this material upon testing with the carbazole (Knutson, C.A. et al Anal. Biochem. 24, 470 (1968)) and the phenol/sulphuric acid (Dubois, M. et al. Anal. Chem., 27 350 (1956)) reagents strongly indicated that the material was not a uronic acid. Methylation analysis of the cell-free indican gave partially methylated alditol acetates consistent with the following fragments being present in the repeating unit: 2 (→3) Glc; 1 (1→4) Man; at least 1 (1→4) Rha. The methylated polysaccharide was reduced ($LiAlH_4$ in boiling tetrahydrofuran for 17 h) and the product was hydrolysed and the resulting fragments were acetylated. A new peak was observed in the gas chromatogram of the acetylated mixture (stationary phase ECNSS-M (Phase Separations Ltd., Queensferry, N. Wales; and U.S. Pat. No. 3,263,401) $T_{TMG}$=3.96). From the mass spectrum of the substance causing this new peak, it was deduced that the structure is as given in Formula (1)

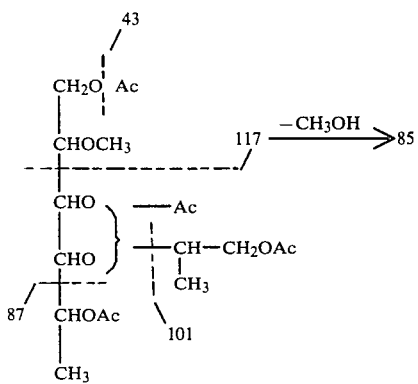

(where the numbers and broken lines indicate the mass spectral fragmentation).

A larger sample of the acidic fraction was obtained and analysed as follows.

The indican sample (6 g) was refluxed with 2 N hydrochloric (100 ml) acid for 7 h. The reaction mixture was cooled and treated with activated charcoal (0.5 h), and filtered through a fluted filter paper. The charcoal residue was thoroughly washed with water and then absolute ethanol and the filtrate and the washings were combined and concentrated by rotory evaporation. The resulting syrup was redissolved in water (30 ml) and re-concentrated (×3) to effect removal of residual hydrochloric acid. The mixture thus obtained was heated for 30 min at 60° C. with triethylamine (2 ml) in water (50 ml) and the cooled solution applied to a column of Amberlite IRA 410 resin (acetate form, 600 ml) and eluted with water (2 x). The acidic components of the hydrolysate were recovered from the resin by washing with 20% acetic acid (900 ml). This solution was concentrated to a syrup which was fractionated by preparative paper chromatography (Whatman3MM, n-butanol:pyridine:water 6:4:3 by volume) into three distinct fractions. The fastest running material (detected by heating the paper strips after spraying with p-anisidine hydrochloride in n-butanol) had a mobility relative to that of mannose ($R_M$) of 1.30, and co-chromatographed with rhamnose. The second fraction had $R_M$ 0.87, in close agreement with the mobility reported (N. K. Kochetkov, et al Carbohydr Res 51 (1976) 229–237) for 3-O-[(R)-1-carboxyethyl]-L-rhamnose in this solvent system ($R_M$ 0.97). The slowest moving spot appeared at $R_M$ 0.42 consistent with the mobility expected for an acidic odisaccharide.

The detection of the above-mentioned reduced methylated derivative and the above-described chromatographic analysis imply that the acid fragment in the repeating unit is a 6-deoxyhexose substituted with lactic acid at either O or O-4 via an ether linkage, and linked to the remainder of the polysaccharide chain through O-4 or O-3 respectively.

Acetyl ester substitution in the polysaccharide was demonstrated by the following experiment. An aqueous solution of indican (500 ml 0.2% w/v) was made alkaline (pH 12) by addition of 10 N sodium hydroxide. After standing at room temperature for 1 hr., concentrated sulphuric acid was added dropwise to lower the pH to 2. This solution was fractionally distilled and the distillate (about 200 ml) after stirring with Amberlite IR120($Na^+$) resin was concentrated to give a white solid. The product was converted into the crystalline S-benzyl thiourea salt; this compound had a melting point (135° C.) identical with an authentic sample of the SS-benzyl thiourea salt of acetic acid. No depression of melting point occurred on admixture of the two. The acetyl content of indican was estimated by the hydroxamic acid/ferric ion complex method to be 12–15% of the polysaccharide.

A sample of purified, essentially cell-free indican prepared as described in Example 4 had a negative specific optical rotation (−61.2°) and a film formed from this material had strong absorbances at 3390, 1735, 1615, 1375, 1250 and 1050 $cm^{-1}$ in the infra-red spectrum. Periodate oxidation studies on de-acetylated cell-free indican showed the consumption of 3–5 moles of periodate per repeating unit, consistent with the structure:

| | |
|---|---|
| 1 → 3 | D-glucose (2 moles) |
| 1 → 4 | Mannose (1 mole) |
| 1 → 4 | Rhamnose (1 or 2 moles) |
| 1 → 3 or 4 | O—(1-carboxyethyl)- rhamnose (1 mole). |

The glucose was shown to be the D-enantiomer by reaction of neutralised, hydrolysates with D glucose-oxidase.

Figure 2:
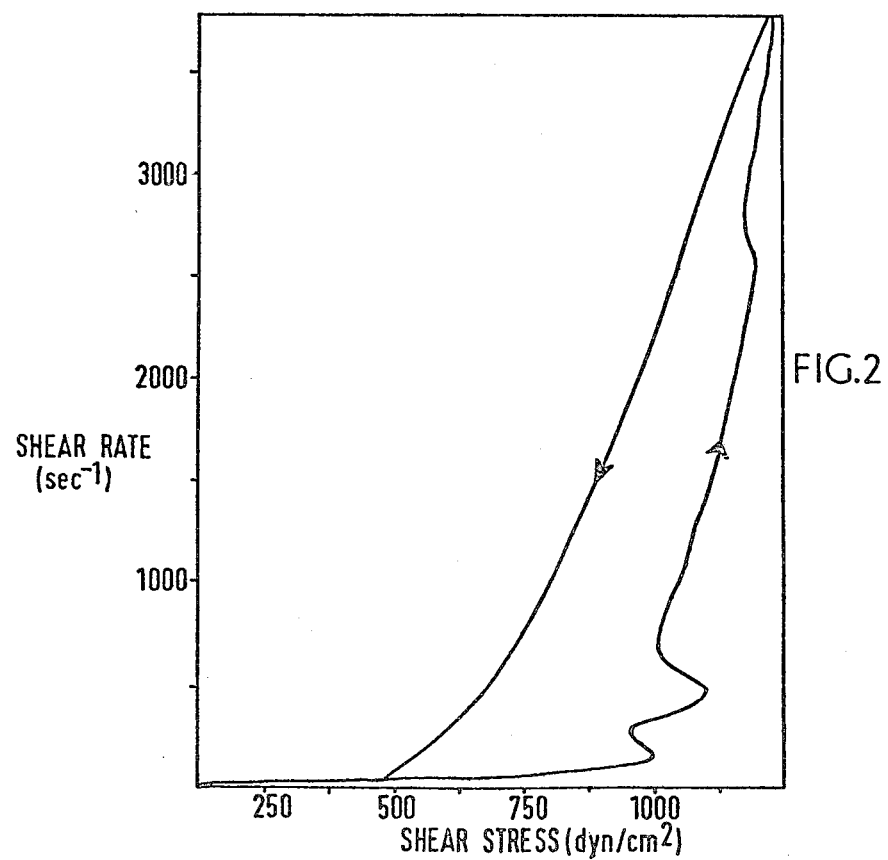

The polysaccharide indican is found to possess an inherent viscosity of about 33.5 dl/g. A useful discussion of viscosity measurement of a substance such as aqueous indican is given by C. Tanford in Physical Chemistry of Macromolecules, published by Wiley & Sons, 1961. For the purposes of this specification, inherent viscosity is taken as the function $$\frac{1}{c} \ln \frac{\eta'}{\eta}$$

where c is the concentration in g/100 ml and $\eta$ and $\eta'$ are the viscosities of the solution at concentration c and the solvent respectively, measured at 25° C. in a $\mu$-tube viscometer. As c tends to zero, the inherent viscosity approaches the intrinsic viscosity [$\eta$]. Measurements for the figure quoted are taken at c=0.01 g/l. FIGS. 1 and 2 in the accompanying drawings illustrate the viscosity characteristics of 1% by weight solutions of indican. FIG. 1 represents the effect of shear stress on shear rate in a 1% aqueous solution, the hysteresis indicating clearly the thixotropic nature of the gel. FIG. 2 is a plot of an equilibrium flow curve of viscosity against the shear rate for a 1% solution in 1% aqueous NaCl, showing thinning with increasing shear.

The polysaccharide produced by *Beijerinckia indica* (Starket and De) was found by J. K. N. Jones, M. B. Perry and W. Sowa, (Canad. J. Chem. 41 2717–2715) and V. M. Parikh and J. K. N. Jones (Canad. J. Chem. 41 2826–2835, 1963) to be quite different from that described above. They claimed the polymer to be linear molecule composed of repeating units of D-glucuronic acid, D-glucose and D-manno-heptose. Later workers, Haug et al., found the uronic acid to be guluronic not glucuronic acid.

EXAMPLE 2

Xanthan Suspension

A solution of the isopropanol-precipitated matter from a culture of *B. indica* ATCC 19361, according to Example 1, was dissolved in methanol to form a 0.8% w/v solution. This solution was diluted with ethanol (0.6 volume) to give a mixture containing 0.5% polysaccharide 37% ethanol and 62.5% methanol. To this gel was added dry xanthan gum to give a mixture with a 20% total solids content. On standing, a smooth gel formed which showed no tendency for the solid to separate out or for syneresis to occur for a period greater than three months. A similar composition containing no indican separated into a liquid and a solid sediment within hours of mixing. The indican-containing preparation dispersed and hydrated rapidly when stirred into water.

EXAMPLE 3

Premium Quality Flat White Paint

The following procedure was carried out, namely the formation of a premix to which were added pigments and resin.

|  | lbs./106.6 gals |
|---|---|
| Premix: (added with vigorous mixing at 1800 rpm.) | |
| water | 47.0 |
| potassium tripolyphosphate | 1.5 |
| tamol 850 (30% solids) (dispersant) | 6.7 |
| indican (0.7% soln.) | 130.0 |
| ethylene glycol | 15.0 |
| hexylene glycol | 35.0 |
| nopco NXZ (antifoaming agent) | 2.0 |
| The following were then added at 1800 rpm. then the speed was increased to 3500 rpm. and the mixture was ground 20 minutes: | |
| titanium dioxide pigment | 300.0 |
| china clay | 75.0 |
| quartz (mean particle size 9 microns) | 70.0 |
| Let-down: (added at low speed mixing) | |
| acrylic latex emulsion (Rhoplex AC-22) (46.5% solids) | 470.0 |
| water | 15.0 |
| bis(phenylmercury)dodecenylsuccinate | 1.0 |
| nopco NXZ | 1.0 |
| indican (0.7% soln.) | 57.0 |
|  | 1226.5 |

Adjust to pH 9.5 with 28% ammonia

EXAMPLE 4

Cell-free Indican

A culture of *Beijerinckia indica* ATCC 19361 on an agar slope was transferred aseptically with 5 ml of Ringers solution into a shake-flask containing 200 ml of sucrose- Burk's medium. After shaking on an orbital shaker at 35° C. for 10 days, the culture had become viscous. It was diluted with three volumes of distilled water and heated at 65° C. for 1 h. The hot solution was centrifuged for 1 h at about 20,000 g to separate the cellular matter. The clear supernatant, on freeze drying gave 0.4 g white fibrous polysaccharide which on dissolution gave a clear, colourless and viscous solution. The cell-free sample of Indican thus prepared had $[\alpha]_D^{20}$ $-61.2°$ (c 0.216 in water).

EXAMPLE 5

| Gelled Pet Food | |
|---|---|
| meat (chunks) | 46% |
| water | 52% |
| benzoic acid | 0.10% |
| sodium metabisulphite | 0.15% |
| indican | 1% |

The partially cooked meat chunks were dispersed in the 2% aqueous solution of indican and heated for 10 min at 80° C. The benzoic acid and sodium metabisulphite were added and the blend was allowed to cool to form a gelled pet food.

EXAMPLE 6

Paint Stripper

A solution of indican in 1:1 methylene chloride:methanol (0.5% by weight) was formed by diluting a 1% methanolic solution of Indican with methylene chloride. The solution was a white, translucent gel which had a texture very suitable for painting onto and adhering to vertical painted surfaces. The solution has the same effectiveness as a hydroxyalkylcellulose-thickened formulation.

EXAMPLE 7

Oil/Water Emulsion

A 0.5% by weight solution of indican in water (100 parts by weight) has added thereto 50 parts by weight of kerosene and the mixture is homogenised. A stable emulsion is obtained. Similarly stability is achieved with salad oil.

EXAMPLE 8

Film

A 1.0% by weight solution of indican in warm water optionally containing glycerol as a plasticiser was degassed and run over a polytetrafluoroethylene sheet and dried for several hours at about 50° C. The resulting film was stripped from the sheet to give a flexible, water-swellable, biodegradable film.

The infrared spectrum of a thin film of indican (without plasticiser) contains a pronounced carbonyl peak at 1730 cm$^{-1}$, which is assigned to the carbonyl of the ester groups (acetate) and a lesser peak at 1610 cm$^{-1}$, which is assigned to the carbonyl of the carboxymethyl groups.

EXAMPLE 9

Liquid Membranes

A water in oil emulsion was made by high shear mixing (Silverson mixer) water (1 volume) into liquid paraffin (3 volumes) containing 2% w/v Span 85. This emulsion (4 volumes) was dispersed into an aqueous solution (3 volumes) of indican (0.5% w/v) using mild agitation (Citenco mixer) to give a smooth water-in-oil-in-water three phase system. Upon standing, the outer thixotropic aqueous phase developed structure which prevented coalescence or separation of the dispersed emulsion. The three phase system could be easily poured and remained visually unchanged after standing for 1 month at room temperature.

Chemicals, such as those used in the pharmaceutical or agricultural industries, could be incorporated into the internal aqueous phase as taught in U.S. Pat. No. 4,083,798.

The advantages of indican-containing formulations of this kind are that they are simpler to prepare, have improved flow characteristics and the use of expensive gelling polysaccharides (e.g. agar) is obviated.

EXAMPLE 10

Ethylene glycol and other non-aqueous solvent gels

A 1% w/v solution of indican in ethylene glycol was prepared by allowing the solid to swell for several hours in the solvent, and then applying agitation. This solution was extremely viscous and appeared to be a weak gel. The gel-like characteristics were increased by heating at 100° C. for 10 min. and allowing the solution to cool. The gel remained unchanged upon standing in the atmosphere for 1 year. Neither was it affected by refrigeration to −20° C.

These properties are of interest in controlling the release of an active compound (e.g. perfume or insect pheromone) or in the preparation of a lubricating mixture.

Similarly gels can be produced in methanol, methanol mixed with methylene dichloride (see Example 6), methanol/ethanol mixtures (see Example 2), and also in ethanol, propan-2-ol, and acetone each containing small (10-20% by volume) proportions of water.

We claim:

1. A method of modifying the viscosity of a liquid by incorporating therein an effective amount of indican, a polysaccharide comprising (1→3) glucose, (1→4) mannose, (1→4) rhamnose and (1→3 or 4) -O-(1-carboxyethyl)- rhamnose units in a molar ratio of about 2:1:1-2:1 respectively, containing 12-15% by weight acetyl units, $[\alpha]_D^{20}$ about −61°, having principle absorption bands in the infra red band at 3390, 1735, 1615, 1375, 1250 and 1050 cm$^{-1}$, a solubility of at least 1% by weight in methanol and in ethylene glycol, and an inherent viscosity of about 33.5 dl/g.

2. A method according to claim 2 using an aqueous fluid.

3. A method according to claim 2 wherein a particulate solid is suspended in an alcoholic medium, by incorporating in the medium an effective amount of indican.

4. A method according to claim 1, wherein the cooking liquor around a meat product or the like is gelled by incorporating therein an effective amount of indican.

5. A pseudoplastic, thickened liquid containing indican, a polysaccharide comprising (1→3) glucose, (1→4) mannose, (1→4) rhamnose and (1→3 or 4) -O-(1-carboxyethyl)- rhamnose units in a molar ratio of about 2:1:1-2:1 respectively, containing 12-15% by weight acetyl units, $[\alpha]_D^{20}$ about −61°, having principle absorption bands in the infra red band at 3390, 1735, 1615, 1375, 1250 and 1050 cm$^{-1}$, a solubility of at least 1% by weight in methanol and in ethylene glycol, and an inherent viscosity of about 33.5 dl/g, substantially free of cells of *B. indica*.

6. A liquid according to claim 5, in which the liquid is aqueous.

7. A liquid according to claim 5, comprising a suspension of a particulate solid in an alcoholic medium.

8. A liquid according to claim 7, comprising a suspension of xanthan gum, alginate or a cellulose in an alcoholic medium.

9. A liquid according to claim 5, comprising an aqueous emulsion of a hydrophobic liquid or of a water-in-oil type of emulsion, containing indican as an emulsifying agent.

10. A liquid according to claim 9, in which the hydrophobic liquid is an oil or petroleum product.

11. A viscosity modified liquid according to claim 5 in the form of a canned food product comprising a jelly containing indican.

12. A liquid according to claim 5, in the form of a paint stripper composition containing a paint solvent together with indican as a thickener.

13. A method according to claim 1, in which an amount of 0.01% to 2% by weight of indican is incorporated in the liquid.

14. A method according to claim 13, in which an amount of from 0.1 to 0.5% by weight of indican is incorporated.

* * * * *